United States Patent
Zhan et al.

(10) Patent No.: US 8,964,183 B2
(45) Date of Patent: Feb. 24, 2015

(54) SYSTEMS AND METHODS FOR SCREENING OF BIOLOGICAL SAMPLES

(75) Inventors: Chun Cheryl Zhan, Niskayuna, NY (US); Juntao Wu, Niskayuna, NY (US); Robert John Filkins, Niskayuna, NY (US); Peter William Lorraine, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 13/485,026

(22) Filed: May 31, 2012

(65) Prior Publication Data
US 2013/0321814 A1 Dec. 5, 2013

(51) Int. Cl.
G01N 21/64 (2006.01)
G01N 21/55 (2014.01)
G01N 21/59 (2006.01)

(52) U.S. Cl.
CPC ............ *G01N 21/59* (2013.01); *G01N 21/6408* (2013.01)
USPC ...... 356/432; 356/445; 250/458.1; 250/459.1

(58) Field of Classification Search
CPC ....... G01N 21/55; G01N 21/59; G01N 21/64; G01N 21/6458; G01N 21/6408; G01N 21/4738
USPC .......... 356/317–318, 326, 432, 445; 359/368, 359/385, 393, 204.1, 35, 22, 197; 250/458.1, 459.1, 200
See application file for complete search history.

(56) References Cited

U.S. PATENT DOCUMENTS

| | | | |
|---|---|---|---|
| 5,127,730 A * | 7/1992 | Brelje et al. .................. 356/318 |
| 5,583,342 A * | 12/1996 | Ichie .......................... 250/459.1 |
| 5,828,051 A * | 10/1998 | Goto ........................ 235/472.01 |
| 6,165,739 A | 12/2000 | Clatch |
| 6,262,838 B1 * | 7/2001 | Montagu ...................... 359/392 |
| 6,376,818 B1 * | 4/2002 | Wilson et al. ............... 250/201.3 |
| 6,388,780 B1 * | 5/2002 | Monaghan et al. ............. 359/35 |
| 6,656,683 B1 | 12/2003 | Reuben et al. |
| 6,741,348 B2 * | 5/2004 | Larsen et al. .................. 356/319 |
| 7,248,282 B2 * | 7/2007 | Maddison ........................ 348/79 |
| 7,277,569 B2 * | 10/2007 | Bruce et al. ................... 382/133 |
| 7,448,995 B2 * | 11/2008 | Wiklof et al. ................. 600/173 |
| 7,468,796 B2 | 12/2008 | Luther et al. |
| 7,474,286 B2 * | 1/2009 | Hajjar et al. .................... 345/81 |
| 7,567,596 B2 * | 7/2009 | Dantus et al. ................... 372/30 |
| 7,899,624 B2 | 3/2011 | Cualing et al. |
| 2002/0154396 A1* | 10/2002 | Overbeck ...................... 359/368 |
| 2003/0034431 A1* | 2/2003 | Mandella et al. .......... 250/201.3 |

(Continued)

OTHER PUBLICATIONS

Attila et al., "Clinical Applications of Laser Scanning Cytometry", Wiley Online Library, pp. 133-143, vol. 50, Issue:3, Jun. 15, 2011.

(Continued)

*Primary Examiner* — Sang Nguyen
(74) *Attorney, Agent, or Firm* — Seema S. Katragadda

(57) ABSTRACT

A screening module configured to screen at least a portion of a biological sample disposed on an analysis surface is provided. The screening module comprises a laser source a scanning unit comprising one or more scanning devices, wherein the scanning devices are configured to rotate in an oscillatory scanning motion about an axis of rotation to scan the analysis surface in at least one direction, wherein the scanning unit is physically coupled to the laser source, and a detection unit comprising one or more detection devices.

16 Claims, 7 Drawing Sheets

(56) References Cited

U.S. PATENT DOCUMENTS

| | | | |
|---|---|---|---|
| 2003/0142934 A1* | 7/2003 | Pan et al. | 385/116 |
| 2003/0156323 A1* | 8/2003 | Overbeck | 359/385 |
| 2005/0059096 A1 | 3/2005 | Pruimboom-Brees et al. | |
| 2006/0187462 A1* | 8/2006 | Srinivasan et al. | 356/479 |
| 2007/0263226 A1* | 11/2007 | Kurtz et al. | 356/492 |
| 2008/0174842 A1* | 7/2008 | Cromwell et al. | 359/197 |
| 2009/0185249 A1* | 7/2009 | Obi et al. | 359/198.1 |
| 2009/0279156 A1* | 11/2009 | Yen et al. | 359/199.4 |
| 2011/0116694 A1* | 5/2011 | Gareau | 382/128 |
| 2011/0147615 A1* | 6/2011 | Kintz | 250/459.1 |
| 2011/0236909 A1 | 9/2011 | Davis et al. | |

OTHER PUBLICATIONS

Georg Erich Steiner et al., "Automated Data Acquisition by Confocal Laser Scanning Microscopy and Image Analysis of Triple Stained Immunofluorescent Leukocytes in Tissue", pp. 39-50, vol. 237 Issues 1-2, Apr. 3, 2000.

Darzynkiewicz et al., "Laser-Scanning Cytometry: A New Instrumentation with Many Applications", The Brander Cancer Research Institute and Department of Pathology, pp. 1-12, vol. 249, Issue 1, May 25, 1999.

* cited by examiner

SYSTEMS AND METHODS FOR SCREENING OF BIOLOGICAL SAMPLES

BACKGROUND

The invention relates to tissue pathology, and more particularly to systems and methods for screening of biological samples.

Laser scanning cytometry (LSC) is used for detecting and measuring various properties of biological samples. Typically, in LSC, a biological sample is stained with a fluorescent dye. The fluorescent dye binds to a particular constituent of a cell in the biological sample. The stained sample is disposed on a slide. A laser source is used to provide focused laser beam to excite the sample. The laser source is coupled to an objective lens to provide a focused laser beam. Fluorescently marked cells when illuminated by the laser beam emit fluorescent light. A detection device is used to measure a fluorescent intensity of the cells in the biological sample. The fluorescent intensity depends on an amount of the fluorescent dye contained in the cell. Based on the fluorescent intensity an amount of a particular cell constituent in the sample is determined.

Conventionally, in LSC systems a whole slide image is formed by acquiring field by field images of individual zones of the slide and then digitally stitching or tiling the individual images together to form a full image. This process of selecting individual images and stitching or tiling them together is time consuming and labor intensive. Existing LSC techniques require about 3 to 5 minutes for preview scanning of a full slide to provide an initial estimate of the constituents present in the slide. Further, conventional microscopes used in LSC require professional personnel to operate the system. The operation of such microscopes is both time-consuming and labor-intensive.

Conventional epi-fluorescent microscope acquisition methods are typically slow and require about an hour or more to produce an image of a whole tissue slide. The conventional epi-fluorescent microscope systems operate with limited prior knowledge of the location or intensity of fluorescent labeling, thereby making such systems inefficient and time consuming.

Typically, LSC systems are bulky and provide lower flexibility to the user. For example, the LSC systems require a narrow field or focused laser beam for scanning the biological sample. Producing a focused laser beam requires complex optics arrangement, stringent alignment requirements for the optics, thereby adding to the size and inflexible nature of the system. Additionally, in the LSC systems the scanning is time consuming because of the relatively narrow field of view of the focused laser beam. Also, with the narrow field of view of the focused laser beam, the probability of the slide surface moving outside the field of view of the focused laser beam is high. Hence, the cell constituent detection may be less than optimal while using the focused laser beam for scanning.

Therefore, it is desirable to have improved systems and methods for tissue screening that provides to identify regions of interest at a high speed in high content cellular analysis and advanced tissue imaging and analysis. Further, it is desirable to have improved systems and methods for tissue screening that are simple to use and easy to align.

BRIEF DESCRIPTION

In one embodiment, a screening module is configured to screen at least a portion of a biological sample disposed on an analysis surface. The screening module comprises a radiation unit, scanning unit and detection unit. The scanning unit comprises one or more scanning devices, wherein the scanning devices are configured to rotate in an oscillatory scanning motion about an axis of rotation to scan the analysis surface in at least one direction. The scanning unit is physically coupled to the radiation unit. The detection unit comprises one or more detection devices.

In another embodiment, a screening system is configured to screen at least a portion of a biological sample disposed on an analysis surface. The screening system comprises a screening module and an imaging unit operatively coupled to the screening module. The screening module comprising a radiation unit, scanning unit, detection unit, signal processing unit and controller unit. The radiation unit comprises one or more radiation sources configured to generate a radiation beam. The scanning unit comprises one or more scanning devices, wherein the scanning devices are configured to rotate in an oscillatory scanning motion about an axis of rotation to scan the analysis surface in at least one direction; wherein the scanning unit is physically coupled to the laser source. The detection unit comprises one or more detection devices, and wherein the detection unit is configured to acquire data representative of one or more constituents of the biological sample. The system further comprises a signal processing unit configured to process data acquired by the detection unit, and a controller unit configured to control a timing relation between the radiation unit, scanning unit, and detection unit.

A method for screening a biological sample comprises providing a biological sample disposed on an analysis surface, providing a focus free or collimated radiation beam, scanning at least a portion of the biological sample using the focus free radiation beam, acquiring a signal representative of constituents of the biological sample, wherein the signal comprises one or more of a fluorescent, absorption signal and scattering signal, and processing the acquired signal to identify regions of interest in the biological sample.

DRAWINGS

These and other features, aspects, and advantages of the invention will become better understood when the following detailed description is read with reference to the accompanying drawings in which like characters represent like parts throughout the drawings, wherein.

DETAILED DESCRIPTION

Figure 1:
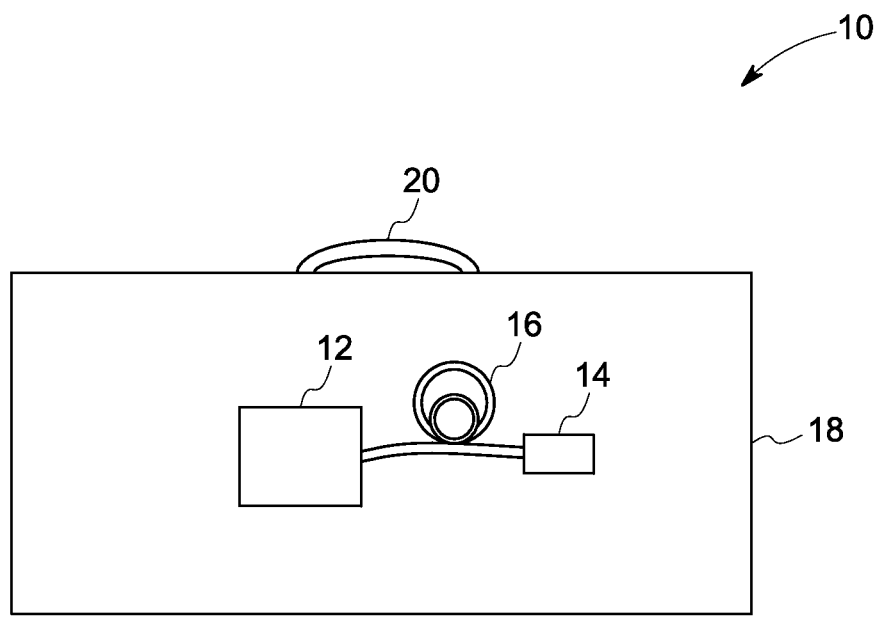
FIG. 1 is a block diagram of an example screening module for screening a biological sample to identify regions of interest.

Embodiments of the systems and methods for screening biological samples provide an initial estimate of constituents present in the biological samples and may also be used for high content cellular analysis to identify regions of interest in the biological samples. The regions of interest may be portions in the sample that demonstrate optical responses such as but not limited to, absorption, fluorescence intensity, scattering, or combinations thereof. The biological samples may comprise solid samples, fluidic samples, samples with regular surfaces, samples with an irregular surfaces, samples with a regular volume, samples with an irregular volume, or combinations thereof. Non-limiting examples of the biological samples may comprise tissue samples, blood samples, body fluids, or combinations thereof.

In certain embodiments, the systems and methods may be configured to pre-screen a biological sample prior to a detailed analysis. The pre-screen may be performed to, for example, identify one or more regions of interest in the sample. The time intensive detailed analysis may be performed for the regions of interest identified in the pre-screening. For example, the cells and tissues disposed in the identified regions of interest may be further imaged or analyzed for diagnostic or research purposes. In one embodiment, the detailed analysis may be performed by another device, such as but not limited to, a microscope imaging unit.

In certain embodiments, a screening module configured to pre-screen a biological sample disposed on an analysis surface may comprise a radiation unit, scanning unit and detection unit. The radiation unit may comprise one or more radiation sources. Non-limiting examples of the radiation sources may comprise a laser source, a light emitting diode, or combinations thereof. The radiation sources may be configured to provide radiation beams to excite at least a portion of the biological tissue sample disposed on the analysis surface. The radiation unit may be configured to provide single or multiple wavelength radiation beams. The scanning unit may comprise one or more scanning devices. The scanning devices may be configured to apply the radiation beams on the analysis surface to excite the biological tissue sample. The scanning devices may be configured to rotate in an oscillatory scanning motion about an axis of rotation to scan the analysis surface in at least one direction. The scanning unit is physically coupled to the radiation unit. In one embodiment, the scanning unit may comprise a two dimensional (2D) scanning device that is configured to scan the analysis surface in at least two directions. The screening module may comprise a detection unit. The detection unit may comprise one or more detection devices, such as but not limited to photo-detectors, to acquire data representative of constituents of the biological tissue sample. In one embodiment, the detection unit may acquire one or more of an absorption signal, a fluorescence signal and a scattering signal from the biological sample. In one example, the acquired signals may be used to determine regions of interest in the biological tissue sample. The screening module may provide high throughput screening for microscopy applications.

In one embodiment, the screening module may be configured to perform high speed screening to identify regions of interest. In one embodiment, the detection unit and scanning unit may not be coupled to each other. For example, the detection unit and scanning unit may not be coupled to each other using a wired or wireless connection. In this embodiment, the detection unit and scanning unit may not communicate with each other and may be configured to operate independent of each other. It has been unexpectedly discovered that the scanning speed of the scanning module may be enhanced by providing an arrangement where the detection unit and scanning unit are not coupled to each other. In one embodiment, independent operations of the detection unit and scanning unit may facilitate high speed screening of tissue samples using the screening module. In some embodiments, the scanning device may perform a scan of the biological sample disposed on the analysis surface in less than or equal to about 1 second.

In one embodiment, the screening module may be operatively coupled to a controller unit. In one example, the controller unit may form part of the screening module. In another example, the controller unit may be separate entity from the screening module that may be operatively coupled to the screening module. The controller unit may be configured to control a timing relation of one or more of the radiation unit, scanning unit and detection unit. For example, the controller unit may be configured to control the scanning speed of the scanning unit in accordance with the detection speed of the detection unit.

In one embodiment, the screening module may be operatively coupled to a signal processing unit. In one example, the signal processing unit may form part of the screening module. In another example, the signal processing unit may be a separate entity that may be operatively coupled to the screening module. The signal processing unit may be in operative association with the detection unit. The data acquired by the detection unit may be transmitted to the signal processing unit. The data may be processed to determine the regions of interest. In one example, the processed data may be displayed to indicate the identified regions of interest. The indicated regions of interest may be further imaged and analyzed using a microscope imaging unit. In one example, the microscope imaging unit may image the regions of interest at a higher resolution, or lower scanning speed, or both, to acquire details of the cell constituents of the tissue portions disposed in the region of interest.

The systems and methods may be used for identifying regions of interest in pathology imaging applications, such as but not limited to, rare cell detection, gene-based tests, such as fluorescence in-situ hybridization (FISH), protein based tests, or combinations thereof, for diagnostic and research purposes. In one example, the determined values for the optical responses may be stored in a memory, for example, a memory of the signal processing unit.

In one embodiment, rare cell detection may comprise detecting rarely occurring cells in peripheral blood streams and body fluids. In one example, it may be desirable to detect and extract rare fetal cells from a maternal blood stream for prenatal care. In another example, it may be desirable to detect cancerous cells in the blood stream. The cancerous cells from malignant tumors may be dispersed in the blood stream. The malignant tumors might otherwise be accessible only through invasive surgical procedures. Detection of cancerous cells of otherwise concealed malignant tumors is highly desirable for early diagnosis of cancer, and for cancer therapy, monitoring, and characterization of a type and stage of cancer. The screening module may be used to pre-scan biological samples for detection of the rare cells.

In another embodiment, the screening module may be configured to perform pre-screening for genetic screening applications. The genetic screening may be desirable for identifying gene alterations in an effective and time efficient manner using the systems and methods. For example, FISH analysis may be performed on biological samples to diagnose Down's syndrome in prenatal applications.

In one embodiment, the screening module may be configured to perform pre-screening for protein-based tests. The protein-based tests may use immunoassays that may detect proteins (e.g., antigens or antibodies). The antigens and antibodies may indicate the presence of an organism in the biological sample. The organism may be friendly (e.g., fetal cells), or unfriendly (a pathogen such as a virus or bacterium).

The systems and methods disclosed may enable cost effective, and time efficient detection. The systems and methods may be configured to allow acquisition of multi-color fluorescence, scatter and absorption data in a wide field of view at high scanning speeds. In some embodiments, the screening module may be configured to scan the analysis surface at a relatively higher scanning speed and lower resolution values to identify regions of interest in a time efficient fashion.

The screening module comprises a small footprint and easy integration to any microscope. The screening module may be a stand-alone unit or add-on module for commercial fluorescent microscope for automated localization of cells and tissue events of interest. The screening module may enable improved imaging speed and efficiency, and simplify the traditional time-consuming and labor-intensive imaging procedure. In one embodiment, slide scanning and analysis may be performed in less than 1 second.

In one embodiment, the screening module may be an automatable unit. In this embodiment, the screening module may identify the regions of interest and communicate data representing the identified regions of interest to another device for detailed analysis. The screening module may be a modular unit that may be selectively operatively coupled to other devices, such as but not limited to a microscope imaging system, a laser scanning cytometer, a flow cytometer, a scanning cytometer, or combinations thereof. In one embodiment, the screening module may be physically coupled to an imaging system. In another embodiment, the screening module may not be physically coupled to the imaging system.

In certain embodiments, a collimated and focus free radiation beam may be used to scan the sample. As used herein, the term "focus-free radiation beam" refers to a radiation beam that is not subjected to focusing optics, such as an objective lens. The focus free beam spans over a greater area as compared to a focused beam. That is, the focus-free radiation beam provides a wide field of view, thereby enabling faster scanning of the biological sample. In addition, the wide field of view of the radiation beam provides sufficient coverage of an area of the biological sample. Also, using the focus free radiation beam eliminates the need for focusing optical elements and associated alignment requirements in a design of the screening module.

In certain embodiments, the screening module may use optical fiber based transmission instead of free space transmission that is typically employed in devices in the field of tissue pathology. In these embodiments, the various components of the screening module, such as but not limited to, the radiation unit, scanning unit and detection unit may be coupled to each other and any other components using an optical fiber. In one embodiment, the radiation unit may be coupled to the scanning unit via a first optical fiber, and the scanning unit may be coupled to the detection unit via a second optical fiber. The optical fiber used to couple different components in the screening module may be the same or different. For example, the first and second optical fibers may be the same or different. The first and second optical fibers may be single mode or multimode optical fibers. Using the optical fiber based transmission instead of free space transmission reduces the size of the device, as the optical fiber requires lesser space. Further, the optical fiber based transmission reduces or eliminates alignment requirements for the components relative to each other. In one embodiment, the optical fiber may be a polymer optical fiber. The polymer optical fiber may comprise a larger numerical aperture thereby facilitating easy laser and signal transfer within the fiber. Further the polymer optical fiber may be flexible, cost effective and easy to handle.

In certain embodiments, the combination of the focus free radiation along with the physical coupling of the components using the optical fiber provides a screening module that entails minimal alignment conditions, and minimal space requirements. Hence, the use of focus free radiation in combination with the optical fiber makes the screening module a high speed, compact module having minimal alignment requirements.

FIG. 1 illustrates an example portable screening module 10 for pre-screening a biological sample disposed on an analysis surface. The module 10 comprises an integrated unit 12 and scanning unit 14. In the illustrated embodiment, the integrated unit 12 comprises a radiation unit (shown in FIG. 2) and detection unit (shown in FIG. 2). Alternatively, the radiation unit may be disposed outside the integrated unit 12. The radiation unit may comprise at least one radiation source. The radiation source may be configured to provide single or multi wavelength radiation beams. In one embodiment, the radiation unit may comprise a collimator operatively coupled to the radiation source to provide collimated radiation. The detection unit may comprise at least one detection device configured to receive fluorescence signals and scattered light from the biological sample upon excitation by the laser beam. In one embodiment, the detection unit may comprise a filter operatively coupled to the detection device to selectively acquire signals from the biological sample.

The analysis surface may be a two dimensional surface, such as but not limited to a glass substrate or a plastic substrate. In one embodiment, the analysis surface may form part of the module 10. In another embodiment, the analysis surface may be disposed outside the module 10.

In certain embodiments, the scanning unit 14 may comprise at least one scanning device. In these embodiments, the scanning device may comprise a micro-electro mechanical system (MEMS) scanning device, galvo mirror scanning device, electronic-controlled liquid crystal scanning device, acoustic optical scanning device, or combinations thereof. The scanning device may be configured to scan the two dimensional (2D) analysis surface. The scanning device may comprise at least one degree of freedom, and may be configured to oscillate the laser beam in at least one direction along the plane of the analysis surface to scan the biological sample disposed on the analysis surface. The scanning device may be a compact device that is configured to scan the radiation beam at a high scanning speed.

In certain embodiments, interaction of the radiation beams with the biological samples result in bioluminescent reactions that typically yield low light intensities, hence, detection devices with relatively higher acquisition properties may be required to detect the biological samples. In one example, the detection devices may comprise one or more of a photomultiplier tube (PMT), avalanche photodiode (APD), semiconductor photomultiplier (SPM), PIN diode, or combinations thereof. In one example, the integrated unit 12 may comprise an array of photomultiplier tubes (PMTs). The detection unit may be configured to acquire and/or display a pixel-by-pixel image of the biological sample. In one embodiment, the array of PMTs may have a one to one correspondence with a pixel array in a display image. In this embodiment, there may be minimal or no manipulation of digital information required for producing the image of the biological sample, thus reducing the processing time.

The integrated unit 12 may be coupled to the scanning unit 14. In one embodiment, the integrated unit 12 may be physically coupled to the scanning unit 14 using an optical fiber. In one example, the radiation source may be coupled to the scanning device using an optical fiber. Further, the detection devices may be coupled to the scanning device using an optical fiber. The optical fibers used to couple the components in the screening module 10 may be the same or different. For example, the radiation source, detection devices and scanning device may be coupled to each other using the same or different optical fibers. Coupling using optical fiber reduces optical losses usually incurred in free space transmission of optical signals. Additionally, coupling using the optical fiber reduces or eliminates stringent requirements related to optical alignment of components in the system. For example, fiber coupling of the radiation source and the scanning device may reduce or eliminate alignment requirements between the radiation source and the scanning device, thus reducing the optical elements required in the module.

The module 10 may be a portable module. The module 10 may comprise a housing 18 that is used to house the various components of the module 10, such as, the integrated unit 12, and scanning unit 14. In one embodiment, the housing 18 of the module 10 may have a compact size. The outer dimensions of the housing 18 may be in a range from about 3 inches×3 inches×3 inches to about 10 inches×10 inches×10 inches. In one example, the housing may be a compact box having a size of 5 inches×5 inches×5 inches.

The housing 18 of the module 10 may comprise provisions, such as but not limited to, a handle 20 for easy handling of the module 10, and for transporting the module 10. However, other provisions such as but not limited to, a strap, wheels that enables moving or transporting the module 10 from one place to another may also be provided. In one example, the module 10 may be transported from one microscope to another.

The module 10 may be configured to be operatively coupled to other imaging system or devices. The module 10 may be configured to be a retro fit device that may be easily integrated with existing imaging systems, such as but not limited to a microscope imaging system, a laser scanning cytometry unit, or other imaging systems or screening modules.

In one example, where the screening module 10 is an automatable device. The pre-screening may be performed on the biological sample. Data from the pre-scan may be processed by the module 10, and information regarding the identified regions of interest may be transmitted to another device, such as but not limited to, a microscope imaging system. The microscope imaging system may then perform the detailed analysis for one or more of the identified regions of interest. In one embodiment, an automated sample dispensing unit for dispensing tissue samples and cells on the slide may be provided.

In one example, the pre-screening of cells and tissues events of interest using the screening module provides flexibility and improved efficiency in high content cellular analysis in tissues. For example, the improved efficiency may be provided by high scanning speed during the pre-scan. Also, the improved efficiency may be provided by preventing detailed analysis of regions that do not comprise cell constituents of interest, that is, regions that are disposed outside the identified regions of interest. The module 10 may provide flexibility in terms of selecting one or more regions of interest from the identified region of interest for further analysis.

Figure 2:
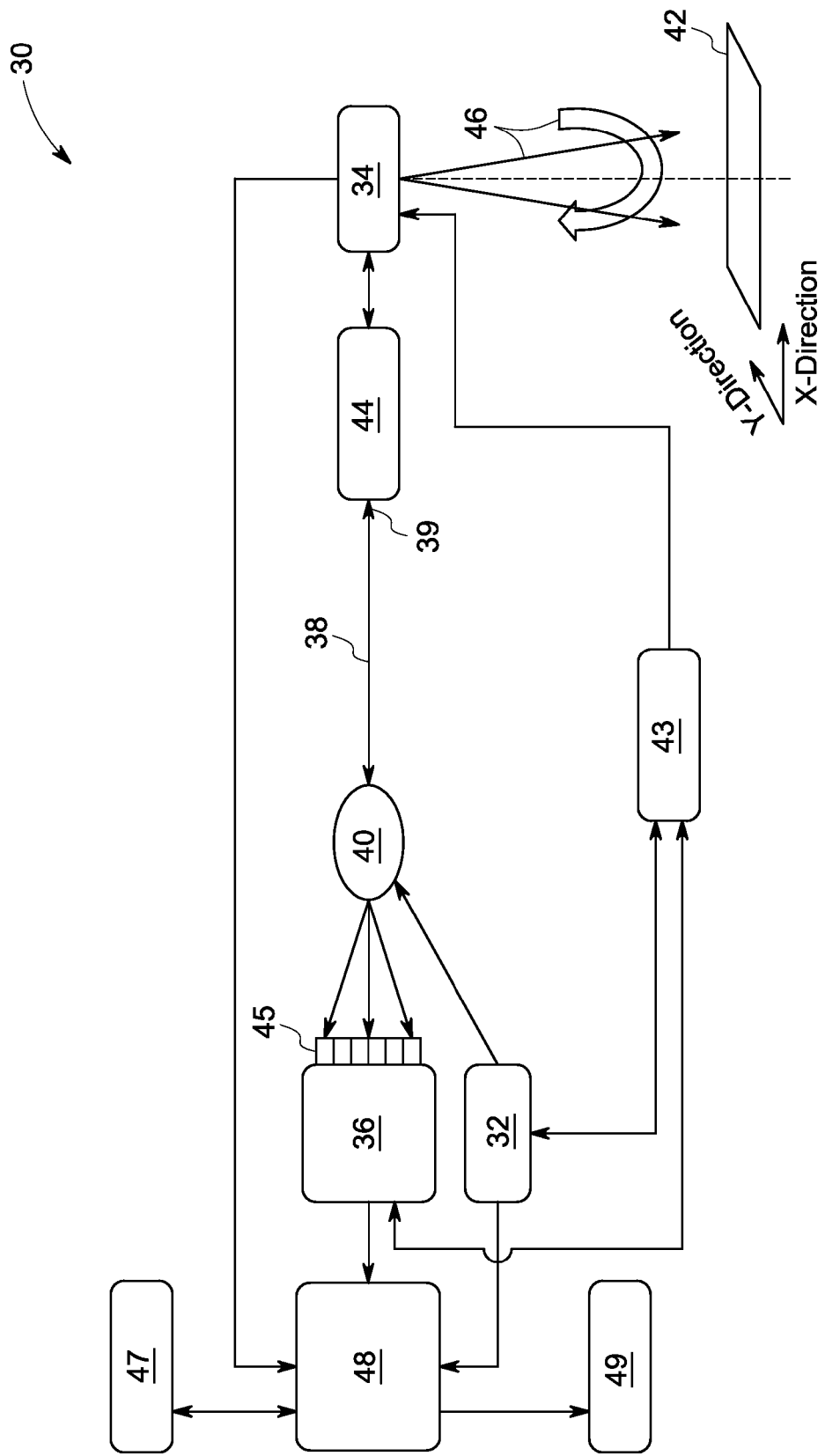
FIG. 2 is a detailed block diagram of an example screening module for screening a biological sample for fluorescence intensity measurements.

FIG. 2 illustrates an example screening module 30 configured to measure fluorescence intensity in a biological sample. In the illustrated embodiment, the module 30 comprises a radiation unit 32, scanning unit 34 and detection unit 36. The radiation unit 32, scanning unit 34 and detection unit 36 may be coupled directly or indirectly to each other using one or more optical fibers 38.

The optical fibers 38 may comprise a plastic or polymer optical fiber. In one embodiment, the optical fiber may comprise a core made of poly(methyl methacrylate) (PMMA), and a cladding made of fluorinated polymers, such as but not limited to, polyperfluorobutenylvinylether.

The optical fibers 38 may be a single mode fiber, a multi-mode fiber, a micro-structured fiber, or a combination thereof. In one embodiment, the multi-mode fiber may comprise a thicker core as compared to the single mode fiber. In this embodiment, the multi-mode fiber may be used to collect light from the biological sample (but may allow for reduced spectral resolution). Single mode fibers may have core diameters in a range from about 1 micron to 10 microns for operation in the visible light region (e.g., 400 nms to 800 nms). The single mode fibers may have a core diameter in a range from about 8 microns to 10 microns for operation in the near infrared region 1100 nms to 1600 nms. It is understood, however, that other diameter fibers may also be used. Micro-structured fibers may comprise a single mode fiber with large core size and large numerical aperture for higher optical collection efficiency with high spectral resolution.

In one embodiment, the optical fiber 16 may have a diameter in a range from about 50 microns to about 1 mm. The optical fiber 16 may have numerical aperture in a range from about 0.2 to about 0.6. It may be desirable to provide optical fiber 16 having minimum attenuation in the visible spectrum, and have high mechanical flexibility and low cost.

The radiation unit 32 may be configured to produce radiation beams that are suitable for exciting the biological sample. The radiation unit 32 may be configured to provide radiation beams comprising one or more wavelengths. The radiation unit 32 may comprise one or more radiation sources. In instances where the radiation source 32 comprises two or more radiation sources, the sources may be selectively turned on and off during the pre-screening and subsequent measurements.

Non-limiting examples of the radiation sources may comprise laser sources, such as but not limited to, collimated laser diode, pulsed laser diode, solid state lasers, optical laser, light emitting diodes, or combinations thereof. In one embodiment, the radiation source may be configured to provide a substantially single wavelength or a narrowband wavelength range, a group of wavelength, or a range of wavelength. In the case of a narrowband wavelength range, a single laser may be used as the radiation source in the screening module. In the case of spectrally broad emissions, two or more radiation sources of different wavelengths may be used by the radiation unit 32. In one example, the radiation beams from the radiation source 32 may illuminate the sample at a plurality of wavelengths to determine the presence and/or concentration of multiple cellular constituents and other features of the cells present in the sample. In one embodiment, multiple wavelengths may be used to excite a variety of fluorescent dyes used to stain the biological sample. For each laser used, there may be a differential absorption of the corresponding radiation beam by the different dyes used to stain the sample. In a case of multi wavelength radiation source, the fluorescence may be excited in the tissue sample in simultaneous or subsequent fashion for different wavelengths.

The radiation unit 32 may be configured to provide radiation beams in a continuous mode or pulsed mode to the biological sample. The continuous or pulsed mode of the radiation unit 32 may be selected based on the kind of measurements that are desirable. For example, a continuous laser beam may be desirable for intensity measurements, while a pulsed laser beam may be desirable for lifetime measurements of the fluorescence from the biological sample.

In certain embodiments, the radiation beams from the radiation unit 32 may be directed at the biological sample using a scanning unit 34 to excite the biological sample. The radiation beams may be routed from the radiation unit 32 to the scanning unit 34 via a compact interrogation device. In one embodiment, the interrogation device may comprise filtering elements, such as a fiber coupler/splitter 40.

In some embodiments, the optical fiber coupler/splitter 40 may be disposed in the optical fiber 38. For example, the optical fiber coupler/splitter 40 may be disposed in the optical fiber that physically couples the radiation unit 32 and the scanning unit 34. In one embodiment, the fiber coupler/splitter 40 may comprise one or more fiber Bragg gratings. In one embodiment, the fiber coupler/splitter 40 may comprise an array of fiber Bragg gratings disposed in the optical fiber 38. The fiber Bragg gratings may comprise patterned periodic variations of the refractive index in the core of the optical fiber. In one example, the periodic variations of the refractive index allows the fiber Bragg gratings to pass the majority of light propagating through the fiber while reflecting back a narrow band of the incident light with a particular peak wavelength (Bragg wavelength). The fiber coupler/splitter 40 having the fiber Bragg grating may be used for coupling or splitting light having particular wavelengths within the optical fiber. The fiber coupler/splitter 40 may provide higher reflectivity for determined wavelengths, and negligible transmission losses for wavelengths other than the determined wavelengths. The fiber coupler/splitter 40 may provide low insertion loss, compactness and cost efficiency. Further, using the fiber coupler/splitter 40 reduces the alignment requirements, which are otherwise needed when using other devices, such as but not limited to, lenses, mirrors, as splitter/devices. For example, since the fiber coupler/splitter 40 is configured to be disposed in the optical fiber 38, there may be minimal or no alignment requirements related to the fiber coupler/splitter 40 and the radiation incident on the fiber coupler/splitter 40.

In one embodiment, the fiber coupler/splitter 40 may be disposed in a single mode or a multimode optical fiber. The fiber coupler/splitter 40 may be disposed or formed in the optical fiber 38 by using processes, such as but not limited to, direct write, phase mask, or other suitable methods that may be employed to selectively write the fiber Bragg gratings in the fiber 38. In one example, gratings that are chirped (e.g. via strain or by using the electro-optic effect) may be used in the fiber coupler/splitter 40.

In certain embodiments, the fiber Bragg gratings may be directly written into the core of the optical fiber 38. In one example, the fiber Bragg gratings may be imprinted into an optical fiber by a holographic process. In another example, the fiber Bragg gratings may be written in the fiber using an ultraviolet (UV) source such as a UV laser. Interference and masking methods may be used in combination with the UV laser to form the fiber Bragg gratings in the optical fiber. The methods used for forming the fiber Bragg gratings depend on the type of grating to be manufactured. In one example, interference method may be used to form the splitter/coupler comprising uniform gratings. In this example, UV laser may be split into two beams which interfere with each other creating a periodic intensity distribution along the interference pattern. In another example, a photo-mask method may be used to form the splitter/coupler. In this example, the photo-mask may be placed between the UV light source and the photosensitive fiber. The shadow of the photo-mask may be used to determine the grating structure based on the transmitted intensity of light incident on the fiber. In one example, point-by-point method may be used to form the splitter-coupler. In this example, a single UV laser beam may comprise a narrow beam that may be equal to the grating period.

In certain embodiments, the radiation beams passing through the fiber coupler/splitter 40 may be received by the scanning unit 34. The scanning unit 34 may be configured to scan the radiation beams across the analysis surface 42. The scanning may be performed in a two-dimensional area.

The radiation beams from the radiation unit 32 may be passed through a collimator 44 to provide collimated radiation beam to the scanning unit 34. In certain embodiments, the collimator 44 may be disposed between the radiation unit 32 and the scanning unit 34. In one embodiment, the collimator 44 may be disposed closer to the radiation unit 32. For example, the collimator 44 may form a part of the radiation unit 32. By way of example, the collimator 44 may be physically disposed on an output end of the radiation unit 32 such that the radiation beams exiting the radiation unit 32 may be passed through the collimator 44. In this embodiment, the collimator 44 and one or more radiation sources of the radiation unit may form an integrated structure. In one example, the collimator 44 may be physically coupled to a laser head to form the integrated structure. The collimated beams may be scanned on the analysis surface 42 using the scanning unit 34.

In another embodiment, the collimator 44 may form part of the scanning unit 34. In these embodiments, the collimator 44 may be physically coupled to a proximal end 39 of the optical fiber 38. In one embodiment, the collimator 44 may be in physical contact with the proximal end 39 of the optical fiber 38. In this embodiment, the collimator 44 may be disposed between the proximal end 39 of the optical fiber 38 and the scanning unit 34. In one embodiment, the collimator 44 may be physically coupled to the proximal end 39 of the optical fiber, thereby reducing alignment considerations. In one example, the collimator 44 may be physically coupled to both the scanning device and proximal end of the optical fiber 38, thereby further reducing the alignment considerations. In one example, the collimator 44 and scanning device may be integrated to form a scanning head. The scanning head may be coupled to the other components, such as the fiber coupler/splitter 40 or the laser source 32 using the optical fiber 38. In one example, the scanning head may be about 8 mm×8 mm×5 mm Additionally, adjacently disposing the proximal end 39 of the optical fiber 38, collimator 44, and scanning unit 34 may help in reducing the overall size of the module due to less space requirements. The collimated radiation beams may be used to scan the analysis surface 44.

The radiation beams may not be passed through a focusing optics. For example, if desired the radiation beams from the radiation unit 32 do not need to be passed through the focusing optics either before or after passing through the collimator 44. The radiation beams received at the analysis surface 42 may be focus free and collimated. The focus free radiation beams may be configured to span over a greater area as compared to a focused beam. Hence, the overall time required to scan the analysis surface 42 may be reduced while providing desirable coverage of the biological sample disposed on the analysis surface 42. The focus free radiation beams do not require the presence of focusing optical elements, such as objective lens, and associated alignment requirements in the module 30 and enable a module with a compact size and reduced alignment considerations.

In one embodiment, the scanning unit 34 may comprise one or more scanning devices, such as but not limited to a MEMS based scanning device, galvo mirror scanner, liquid crystal digital scanner, acoustic optical scanner, or a combination thereof. The scanning device may be selected based on one or more of a space, speed and cost criterion for the portable module 30. For example, the liquid crystal scanner may be selected for a very compact module. Similarly, a MEMS based scanning device may be employed for fast scanning speed. In one embodiment, a scanning speed of the scanning device may be in a range from about 15 KHz to about 30 KHz. In one example, the MEMS based scanning device may have a scanning speed of up to about 20 KHz.

In certain embodiments, the scanning device may be configured to scan the two dimensional (2D) analysis surface. The scanning device may be configured to scan the analysis surface in one or more directions. The number of scanning directions may be determined based on a shape of the analysis surface 42 and radiation beam that is being used for scanning the analysis surface. For example, for a 2D analysis surface a point radiation beam may be scanned in two directions by the scanning device. Similarly, for a 2D analysis surface, a line radiation beam may be scanned in one direction to scan the entire analysis surface. In the illustrated embodiment, as generally represented by reference numeral 46, the scanning device may oscillate the laser beam in two different directions (e.g., x- and y-directions) along the plane of the analysis surface to scan the tissue sample disposed on the analysis surface. In one example, the MEMS based scanning device may comprise a resonator having two degrees of freedom. In one example, the scanning angle of the scanning device may be in a range from about −30 degrees to +30 degrees in the two directions across the analysis surface. In another example, the scanning angle of the scanning device may be in a range from about −15 degrees to +15 degrees in two directions across the analysis surface.

In one embodiment, the analysis surface 42 may be disposed on a sample stage (not shown). The sample stage may be configured to undergo a translational or rotational motion. The motion of the sample stage may be complementary to the scanning direction of the scanning unit 34. In one example, if the scanning unit 34 is scanning in the x-direction, the sample stage may be configured to move along the y-direction so as to effectively cover the area on the slide.

The biological sample disposed on the analysis surface 42 may provide excitation signals in response to being irradiated by the radiation beams. The detection unit 36 may be configured to detect the excitation signals, such as but not limited to, fluorescence signals, absorption signals, scattering signals from the biological sample, and generate a detectable signal in response to the detected excitation signals.

The detection unit 36 may comprise one or more detection devices configured to detect signals from the biological samples. The detection unit 36 may be configured to register a lifetime of the fluorescent signal, or scattering signal, or combinations thereof. The detection devices may be configured to multiply the current produced by incident light, thereby enabling individual photons to be detected even at lower levels of the incident flux of light.

In one embodiment, a detection device may comprise an avalanche photodiode (APD). In one embodiment, the APD detection device may have an internal current gain effect (around 100) due to impact ionization (avalanche effect). In another embodiment, the APDs may use alternative doping and beveling techniques to allow greater voltage to be applied (e.g., voltage greater than about 1500 V) before breakdown is reached and hence a greater operating gain (e.g., gain greater than about 1000). In one embodiment, a single-photon avalanche diode (SPAD) may be used as the detection device. The SPAD detection device may be configured to operate with a reverse bias voltage above the breakdown voltage. In another embodiment, a PIN diode is used as a detection device. In one embodiment, a PMT based detector may produce photoelectrons at the PMT photocathode in response to the fluorescence photons.

In another embodiment a silicon photomultiplier (SPM) may be configured to detect the excitation signals. The SPM may be configured to detect lower levels of fluorescence signals. The SPM may be suitable due to its small size, low bias voltage, insensitivity to magnetic fields, and immunity to damage from light overexposure. SPM sensing and signal processing units may be suitable for rapid detection of small-volume samples at a low cost, thereby satisfying the requirements for the module. Further, SPM provides uniform gain in response to the photons received.

In one embodiment, a suitable detection device may be selected based on the type of measurement, scanning speed, size of the module and cost considerations. For example, for smaller size screening modules 30, APD, SPM and PMT may be desirable, whereas for higher scanning speed, it may be desirable to use PIN detection devices. The APD detection devices may be suitable for lower costs. The detection devices may also be selected based on the dye used to prepare the biological samples for screening. For example, for dyes with longer lifetime or higher fluorescence intensity lower speed detection devices, such as APDs may be used.

In one embodiment, the detection unit 36 comprises an array of PMTS. The size of the PMT arrays may be adjusted to correspond to the size of the biological sample disposed on the analysis surface or the size of the analysis surface itself. In certain embodiments, the detector unit comprising the PMT based detection devices may have a high data read-out rate, which facilitates the tissue sample to be scanned at a fast scanning speed. In one example, the PMT based detection devices may generate an electric output within a few nanoseconds of a photon striking a photocathode of the PMT.

In one embodiment, a collection efficiency of the fluorescent light may depend on the numerical aperture of the optical fiber used to couple the scanning unit 34 to the detection unit 36, and may increase with the increase in the numerical aperture of the optical fiber.

In certain embodiments, filters 45 may be used in combination with the detection devices for multiple wavelength detection. In the case of an array of detection devices, each detection device may be coupled to a corresponding filter to receive desirable wavelength from the excitation signals.

The screening module 30 may further comprise a controller unit 43. In certain embodiments, the controller unit 43 may be configured to produce coordinated operation of the radiation unit, scanning unit, and detection unit. In one embodiment, the controller unit 43 may be configured to control a timing relation between the radiation source, scanning device and the detection devices. In one embodiment, the detection unit 36 may not comprise filters, and color isolation may be achieved via the controller unit 43. For example, the controller unit 43 may selectively control a delay time of the detection unit 36 such that the delay time of the detection unit 36 lies within the lifetime of the signal decay in the biological sample.

The screening module 30 may further comprise a signal processing unit 48 for processing the signals acquired by the detection unit 36, where the signals are representative of the constituents of the biological sample. The output of the detection devices may be registered and processed by the signal processing unit 48. In certain embodiments, the signal processing unit 48 may comprise a microprocessor, microcontroller or a digital signal processor (DSP), field programmable gate array (FPGA), or a combination thereof. The system 10 may also comprise a storage device for at least temporarily storing one or more images or information regarding regions of interest. The storage device may comprise, but is not limited to, any suitable hard drive memory associated with the processor such as the ROM (read only memory), RAM (random access memory) or DRAM (dynamic random access memory) of a CPU (central processing unit), or any suitable disk drive memory device such as a DVD or CD, or a zip drive or memory card. The storage device may be remotely located from the signal processing unit 48, and yet still be accessed through any suitable connection device or communications network including but not limited to local area networks, cable networks, satellite networks, and the internet, regardless whether hard wired or wireless. In one embodiment, the embedded DSP function of FPGA may generate individual images of scattering, and fluorescence at different wavelengths, simultaneously. In one embodiment, the signal processing unit 48 may comprise an embedded analysis algorithm, which provides evaluation of the bio sample based on determined parameters.

A display device 47, such as but not limited to a monitor, liquid crystal display, computer, or a combination thereof, may be used to display screening data comprising results from the pre-screening.

A user interface 49, such as, but not limited to, a graphical user interface (GUI), keyboard, mouse, touchscreen, may be used to allow the user to interact with the screening module 10. In one embodiment, the user may select the type of measurement, such as but not limited to, intensity measurement, lifetime measurement, or the spectra measurement.

In one example, the screening module 30 may be configured to perform automated analysis for example, for high content cellular analysis and advanced tissue imaging/analysis. The combination of high frequency response, high gain, low noise, high-sensitivity, and large area of collection of the screening module 30 are suitable for the pre-screening applications.

In certain embodiments, the module 30 may be computer-operated or automated. For example, software may determine, among other things, the number of scans, the kind of measurement. The data representative of the regions of interest may be automatically transmitted to other imaging device, such as a microscope imaging system.

The screening module 30 may be configured for simultaneous acquisition of multiple fluorescence intensity, spectra and lifetime. The screening module 30 may be configured to provide fast speed, white field images at the rate of less than 1 second per sample or slide. In certain embodiments, the pre-screening may be performed to obtain wide field of view scan of tissue samples. In one example, discrete locations distributed over wide areas of the analysis surface may be imaged using the wide field of view scan. A typical microscope slide may have an area of about 2.5 cm×7.5 cm.

In certain embodiments, the screening module may be configured to perform high speed screening of the biological sample. The high speed screening may be enabled via the combination of focusing-free radiation source, high speed detection unit, and fast signal processing unit. Due to the fast screening rate, the screening data may be provided in real-time. In one example of the screening module, the radiation unit may comprise a laser source, the scanning unit may comprise a MEMS-based 2D scanner, and the detection unit may comprise an array of PMTs. In one embodiment, the PMT array may have a rise time of less than about 1 nanosecond. In one embodiment, the screening module may be used for screening the biological sample at a screening frequency of about 20 KHz. In one embodiment, the resulting imaging frame rate for the scanning is above 30 frames per second. In this example, the high imaging frame rate may be reached while acquiring simultaneous images of scattering and fluorescence at different wavelength.

Figure 3:
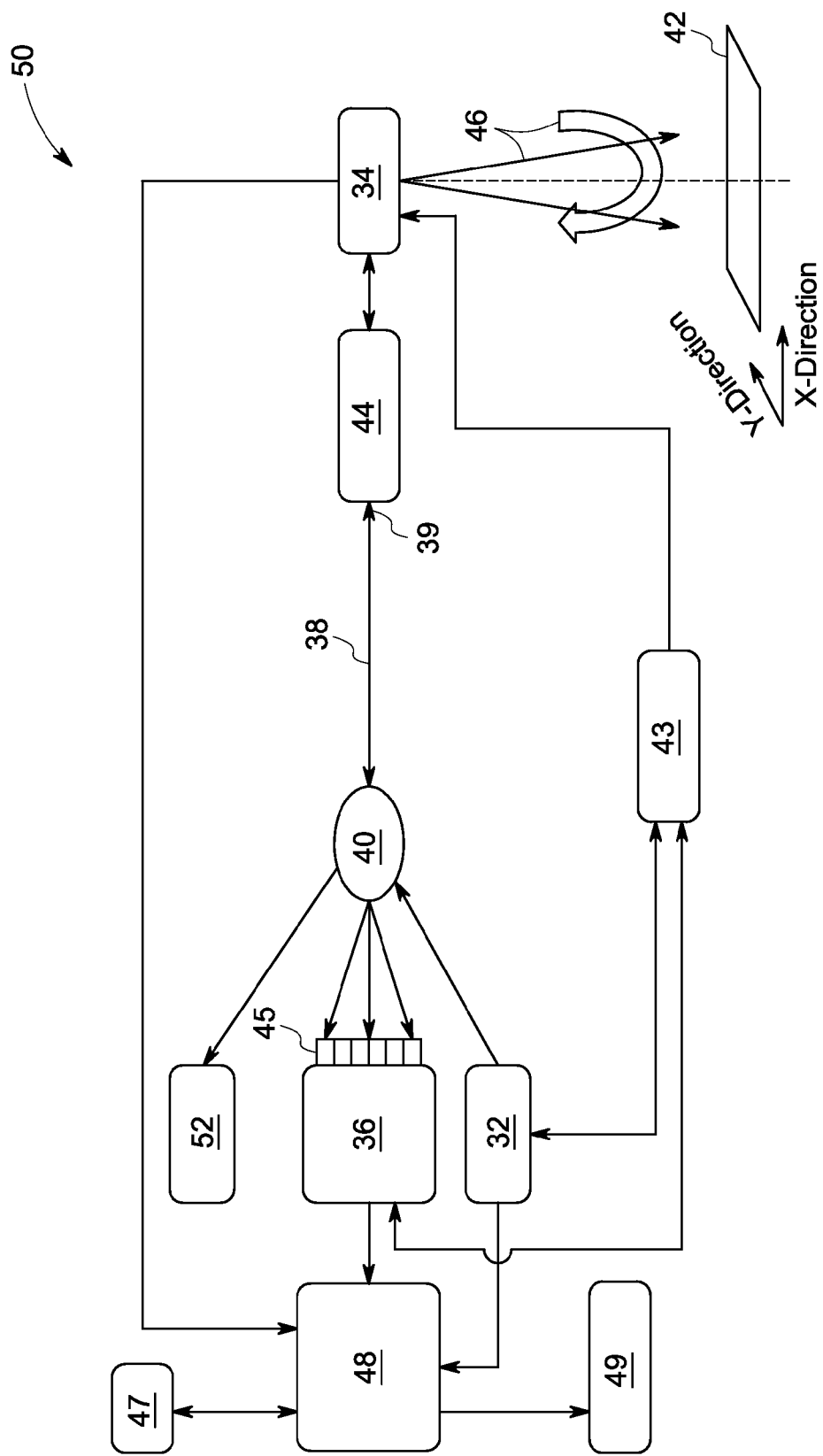
FIG. 3 is a block diagram of an example screening module for screening a biological sample for fluorescence spectra measurements.

FIG. 3 illustrates an example screening module 50 configured to measure fluorescence spectra of a biological sample. In one embodiment, a spectrometer 52 may be coupled to one arm of the fiber coupler/splitter. This arrangement may be a convenient retrofit that may be coupled to screening modules. The lifetime of the fluorophore signal may be measured using a detection device to create the fluorescent lifetime image of the entire slide.

Figure 4:
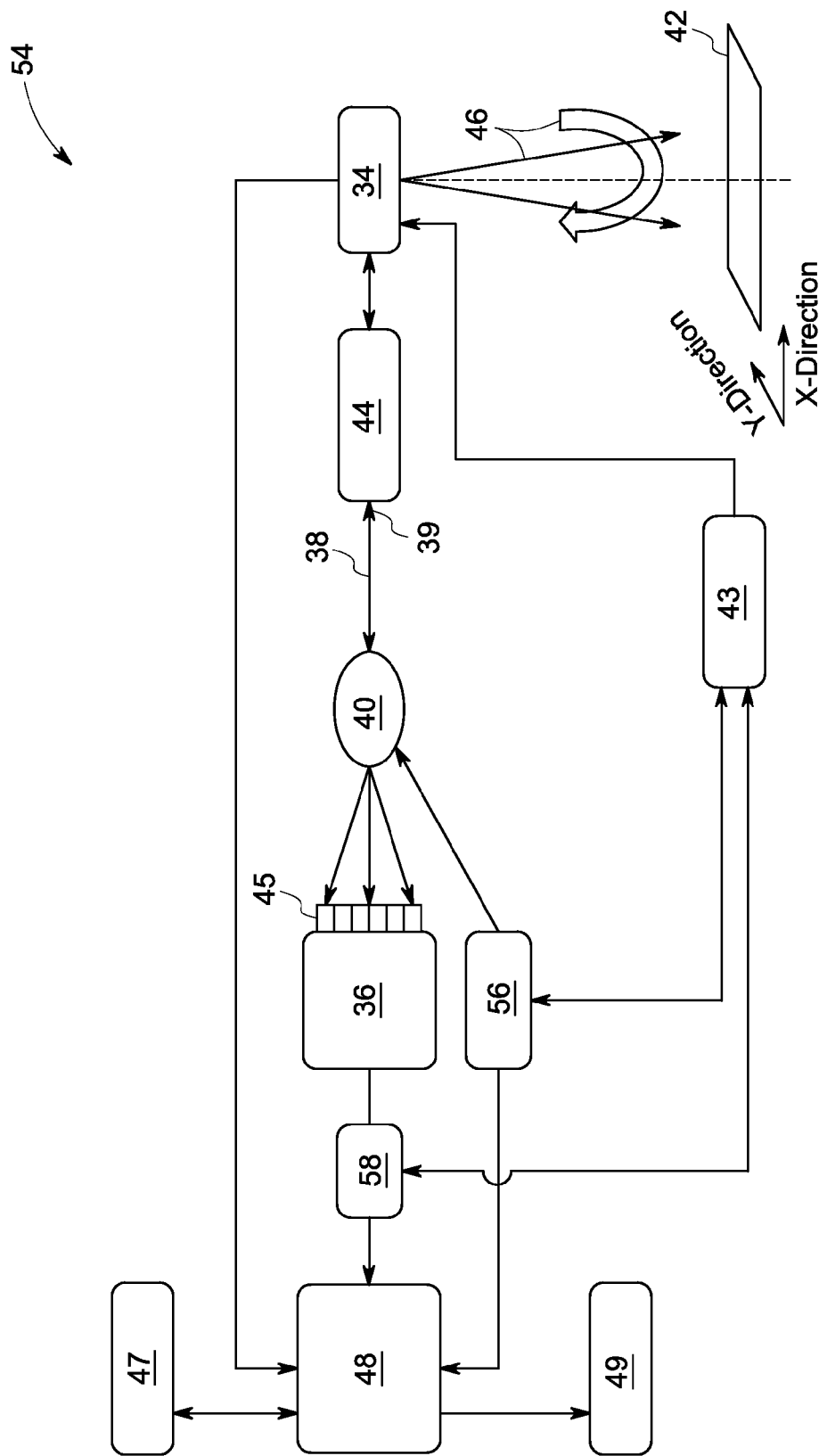
FIG. 4 is a block diagram of an example screening module for screening a biological sample for fluorescence lifetime measurements.

FIG. 4 illustrates an example screening module 54 configured to measure fluorescent lifetime of a biological sample. In one embodiment, a pulsed laser 56 may be used along with a photon counting device, such as but not limited to, a time correlated single photon counting (TCSPC) unit 58. Detection devices having a response time in a range of a few nanoseconds may be used in the scanning module 54. The TCSPC unit 58 may be detachably coupled to the module 54. In one embodiment, the TCSPC unit 58 may be detachably coupled to the module 54 using a USB interface.

Figure 5:
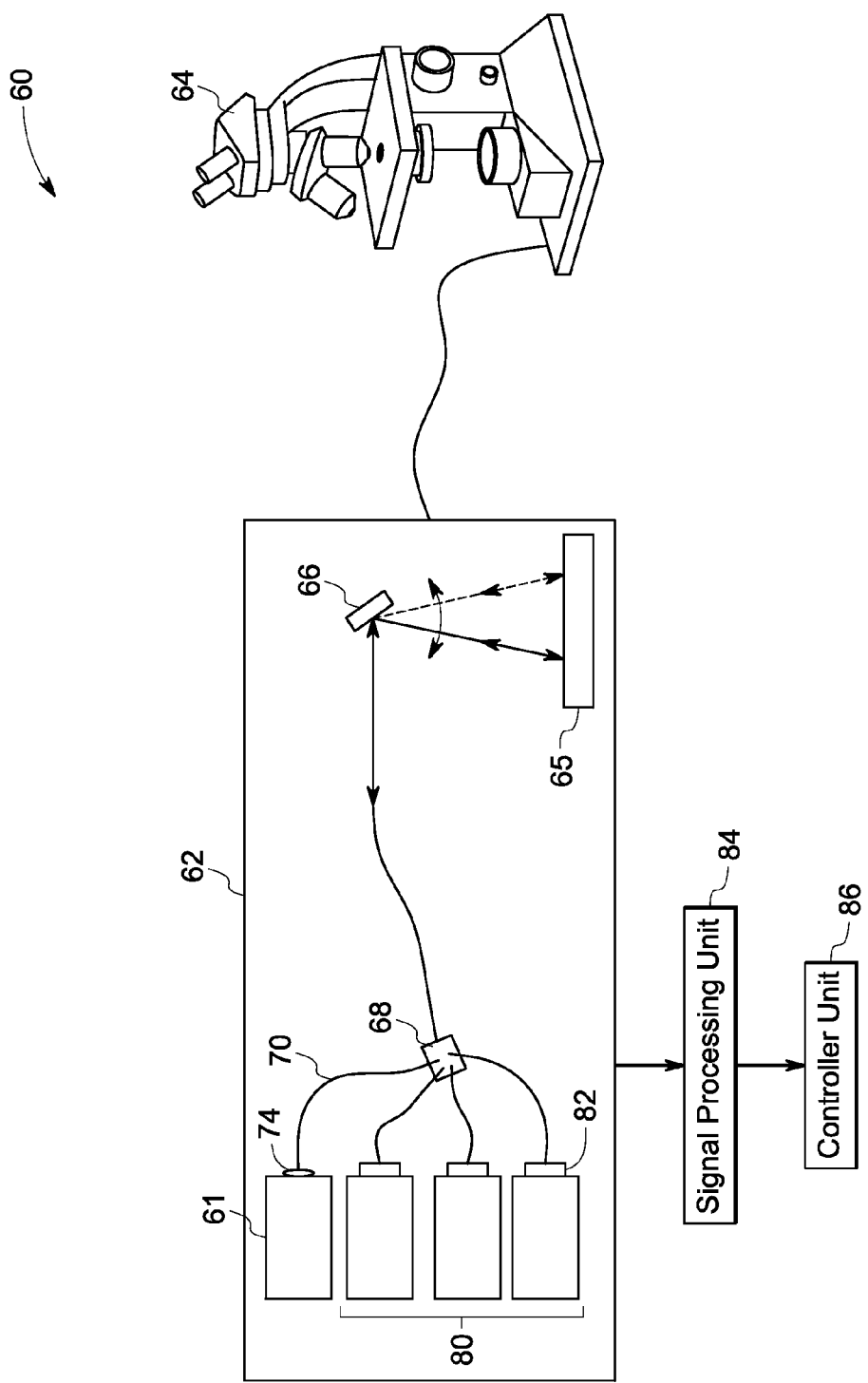
FIG. 5 is a block diagram of an example screening system comprising a screening module configured to be operatively coupled to other imaging system.

FIG. 5 illustrates an example of a screening system 60 where a screening module 62 is operatively coupled to a microscope imaging module 64. In one embodiment, the microscope imaging module 64 may comprise one or more of the transmission microscope, and reflectance microscope. In the transmission microscope, the detector may be configured to illuminate a spot on the object being viewed, and a detector system is disposed on the opposite side of the object being viewed. In the reflectance microscope, the detector may be configured to receive the light reflected from the region being illuminated by the laser beam on the slide.

The system 60 is configured for fast preview scanning, and sequential analysis of biological samples. The system comprises the screening module 62 for pre-screening a biological sample, and a microscope imaging module 64 for performing detailed scanning and analysis of regions of interest identified during the pre-screening. The fast preview screening may be desirable in microscopy applications to perform the analysis in a time efficient manner by saving time on detailed analysis of regions that are not of interest.

In one embodiment, the screening module 62 may be physically coupled to the microscope 64. In this embodiment, the screening module 62 may be detachably coupled to the microscope 64. In one embodiment, the screening module 62 may be coupled to the microscope 64, and the connection may be activated on a need basis. In one embodiment, a switch may be provided to activate the connection between the connection between the module 62 and the microscope 64. In this embodiment, the tissue sample may be disposed on an analysis surface 65. A radiation source 61 may be turned on to provide single or multi wavelength radiation beams. The radiation beams may be directed to a scanning device 66 via a fiber coupler/splitter 68 using the optical fiber 70. The fiber coupler/splitter 68 may be disposed in the optical fiber 70. In one embodiment, the fiber coupler/splitter may comprise a grating device that may be disposed in the optical fiber 70.

The analysis surface 65 may be disposed on a sample stage. The sample stage may be shared by the screening module 62 and the microscope 64. Alternatively, the screening module 62 and the microscope 64 may comprise separate sample stages.

The scanning device 66 may be configured to scan the radiation beams on the analysis surface 65. In one embodiment, the radiation source 61 may be operatively coupled to a collimator 74 to provide collimated laser beam to the scanning device 66 for scanning the biological sample. In another embodiment, the scanning device 66 and the collimator 74 may be integrated to form a scanning head that is configured to scan the radiation beam on the tissue sample. The collimated beam is directly scanned across the sample slide without pre-focusing or any other adjustment, thereby significantly expediting the scanning procedure.

The emitted signals, such as but not limited to fluorescence signals, absorption signals, or scattering signals, may be received by detection devices 80. In one embodiment, the fluorescent emissions and scattering signals from the tissue sample may be collected using an optical lens (not shown) having a relatively large numerical aperture. In one example, the numerical aperture of the lens 82 may be in a range from about 0.1 to about 3.3. The fluorescent emissions and the scattering signals may be directed to the detection devices 80 via the scanning device 66 and the fiber coupler/splitter 68. Undesirable radiation may be filtered out using filters 82 which are disposed on receiving ends of the detection devices 80. The output of the detection devices 80 may be applied to an analog to digital converter (A/D).

The acquired image may be processed using a signal processing unit 84. The radiation source 61, scanning device 66, and detection devices 80 may be controlled using a controller unit 86. Further, a user interface may be used to allow the user to interact with the scanning system 60.

Figure 6:
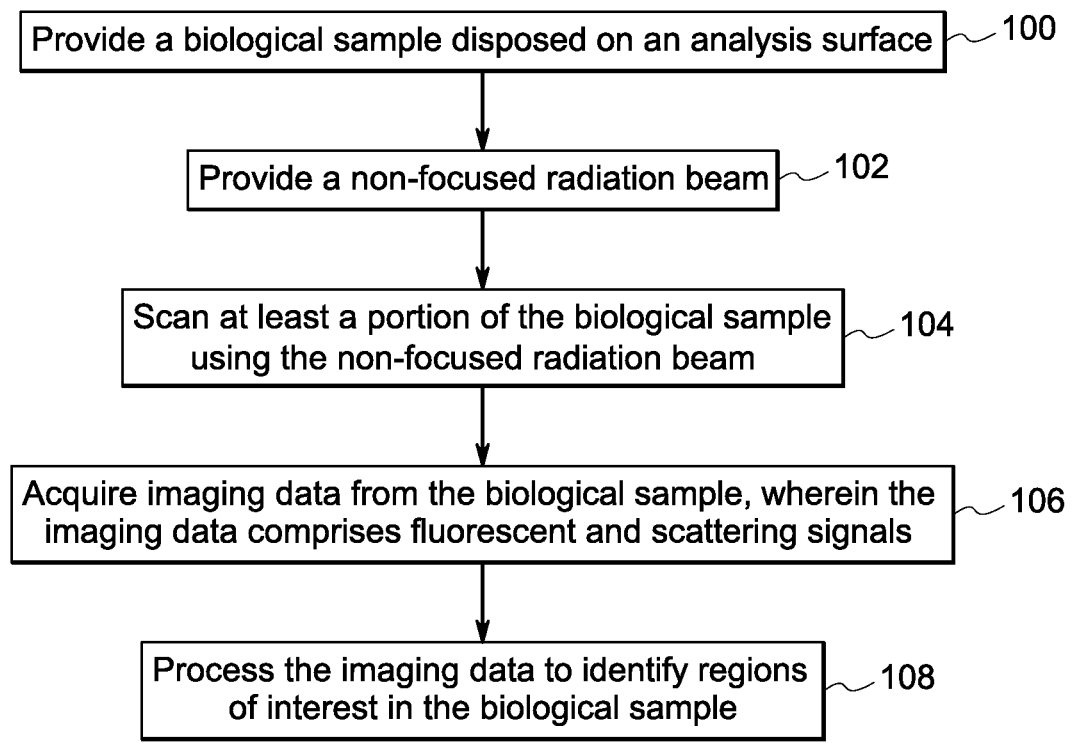
FIG. 6 is a flow chart of an example method for screening a biological sample to identify a region of interest.

FIG. 6 illustrates a flow chart for the method of use of the scanning module. At step 100, a biological sample is provided. The biological sample may be disposed on an analysis surface. In one embodiment, cells from a sample may be rinsed in a suitable buffer, and then stained with anti-bodies responsible for fluorescence. After antibody staining, the cells may be disposed in a suspension medium. In one embodiment, the suspension medium may be a gelatable and polymerizable medium.

In one embodiment, the sample stage may be the stage of the microscope. In one embodiment, the sample stage may be configured to undergo translational motion to enable scanning of the analysis surface by the laser beam.

At step 102, a focus free and collimated radiation beam may be provided. The focus free radiation beam may facilitate wide field of view screening of the biological sample. The focus free and collimated radiation beam may be produced by passing the radiation beam through a collimator. The focus free radiation beam does not require the radiation beam to be passed through a focusing optics.

At step 104, the tissue sample may be scanned using a focus free, collimated laser beam. The scan may be a line or pixel scan. By adjusting the step size of the scan, the scan resolution may be adjusted. In one embodiment, the screening module may be configured to operate at low resolution and high speed scan for the biological sample.

In one embodiment, the tissue sample may be first scanned with radiation of a determined wavelength, and then the same scan area may be scanned with radiation of another wavelength different from the determined wavelength. In one embodiment, the data from two or more such scans may be combined.

At step 106, the excitation signals from the analysis surface may be acquired. At step 108, the data collected during the pre-scan may be processed to identify regions of interest. Optionally, the processed data representing the regions of interest may be displayed. In one embodiment, the processed data may be stored, or transferred to the device conducting the detailed analysis. In one embodiment, the processed data may be stored on a hard disk or read-write magneto optic disk, or transmitted to the device using data line or wireless communication medium. The device may then perform detailed analysis of the regions of interest. Detailed analysis may be performed at high resolution, The entire process may be automated. The system may be controlled or commands may be provided using a computer. After placing the tissue sample on the analysis surface, commands from a processor and/or controller may be embedded in the system to accept the sample and scan/pre scan the same. Alternatively, the system may be provided with a switch, such that when the system is switched on, the scanning begins. In one embodiment, the output of the system may comprise an image of the analysis surface, with the regions of interest marked. In one example, the output may be communicated to the microscope, which may then perform detailed analysis on the regions of interest. A stage for disposing the analysis surface may be the same or different for the screening module and the microscope.

Experiment

Figure 7:
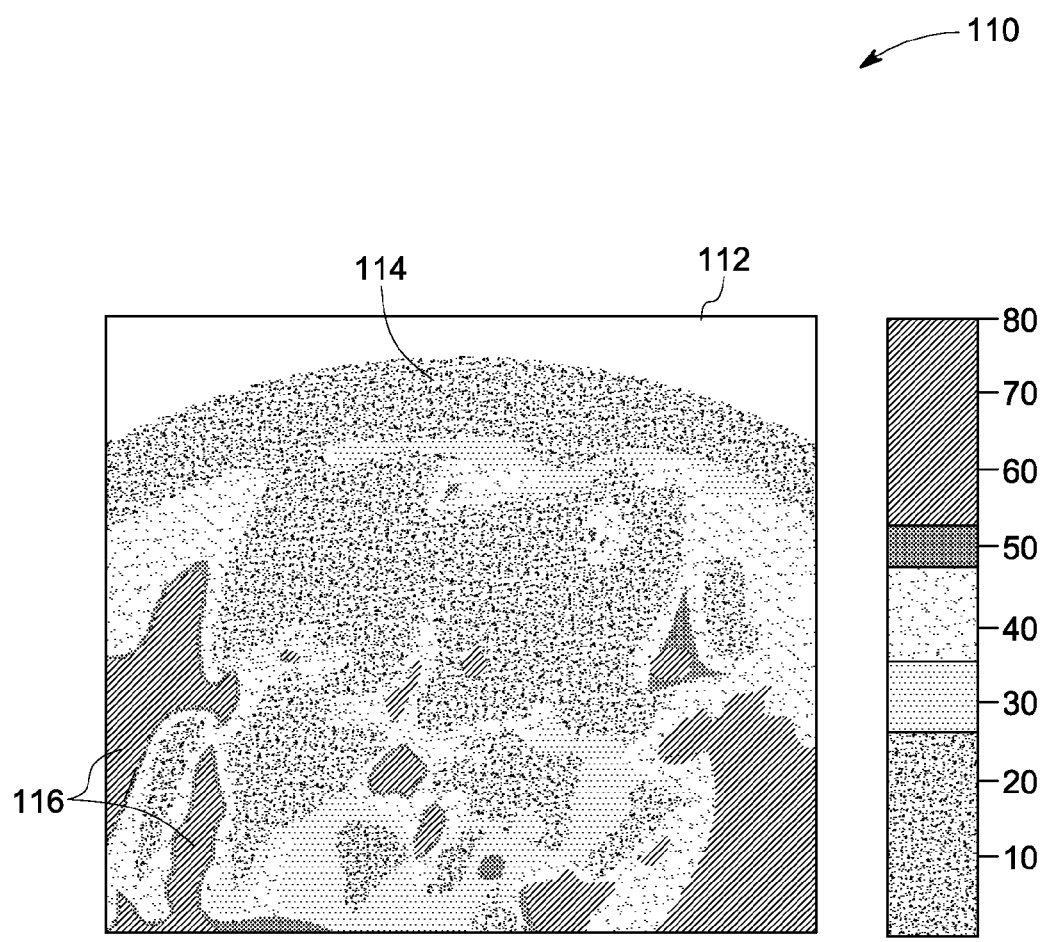
FIG. 7 is an example image from pre-screening using a screening module.

FIG. 7 illustrates an image 110 of rat epithelial tissues obtained using the screening module of the disclosure. Scattering signals are used to obtain the fluorescence image of the tissues. The different constituents of the tissues were indicated in the pre-screening as represented by reference numerals 112, 114 and 116. The rat epithelial tissues were stained using Cy5 dye. The sample is prepared by fixing the rat epithelia tissues using 10% neutral buffered formalin obtained from Sigma-Aldrich (St. Louis, Mo. 63103). Subsequently, the rat epithelial tissues are de-hydrated, and embedded in paraffin wax, and sectioned with a microtome, and disposed on a glass slide. The glass slide is then heated at a temperature of about 60 degrees C. for about 1 hour. The tissues are then re-hydrated, and undergo a process of antigen retrieval. The antigen retrieval comprises using two different solutions (low pH—citrate, followed by high pH—Tris obtained from Sigma-Aldrich at variable temperatures for 20 minutes each in a pressure cooker (Biocare decloaking chamber plus, Biocare Medical Concord, Calif. 94520). The slides are then blocked to facilitate reduction of non-specific binding of the antibody, overnight at 4 degrees C. in a solution consisting of 3% BSA, 10% Donkey Serum in 1×PBS, and stained using Cy5 obtained from Sigma-Aldrich.

In certain embodiments, the screening module may be used for high throughput cell analysis, multiple fluorophores, and high content screening. In one example, the screening module may be configured to perform high sensitivity and high speed scanning to identify the regions of interest. Rather than randomly imaging an entire field (like in a microscope imaging system), pre-screening enables selecting regions of interest in a tissue sample for further analysis. The screening module may be configured to identify the regions of interest for a subsequent high resolution scan, thereby saving time by preventing examination of regions that are not of interest. Second, the tissue scanning module uses optical fiber coupling in place of free space transmission, which provides compact size and reduces or even eliminates alignment requirements otherwise required. Further, the screening module does not require focusing the laser beam. Accordingly, the screening module does not require focusing optics and corresponding alignment requirements. The absence of focusing optics and their alignment requirements, and associated challenges, such as aberration, makes the screening module compact and easy to handle. Accordingly, the screening module may be realized in a very simple manner with respect to engineering and is particularly simple to handle with respect to application.

In certain embodiments, images indicating the regions of interest may be provided in real-time by the screening module. Simultaneous acquisition of multiple fluorescence intensity, spectra and lifetime may be achieved by the screening module. Absence of a need to focus and align significantly reduces processing times. Fast speed (greater than about 30 frames per second) and a wide-field of view enable scanning and imaging in a time efficient fashion while reducing the risk of human error.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A screening system configured for fast screening and analysis of at least a portion of a biological sample disposed on an analysis surface, the screening system comprising:
   a screening module configured for fast screening, comprising:
      a radiation unit comprising at least one radiation source, wherein the at least one radiation source is not coupled to focusing optics to provide a focus-free radiation beam having a wide field of view;
      a scanning unit comprising one or more scanning devices, wherein the one or more scanning devices are configured to rotate in an oscillatory scanning motion about an axis of rotation to scan the analysis surface in at least one direction, and wherein the scanning unit is physically coupled to the radiation unit;
      a detection unit comprising one or more detection devices; and
   a microscope imaging module comprising a transmission microscope, a reflectance microscope, or both.

2. The screening system of claim 1, wherein the radiation unit comprises a pulsed laser, a collimated laser, a continuous laser, a light emitting diode, or combinations thereof.

3. The screening system of claim 1, wherein the radiation unit comprises a pulsed mode radiation source, a continuous mode radiation source, or both.

4. The screening system of claim 1, wherein the detection unit comprises photomultiplier tubes, avalanche photo diodes, pin junction diodes, silicon photo multiplier tubes, single-photon avalanche diodes, or combinations thereof.

5. The screening system of claim 1, wherein the detection unit comprises an array of detection devices.

6. The screening system of claim 1, wherein the radiation unit is physically coupled to the scanning unit via a first optical fiber, and wherein the scanning unit is physically coupled to the detection unit via a second optical fiber.

7. The screening system of claim 6, further comprising one or more filtering elements disposed in the first optical fiber, the second optical fiber, or both.

8. The screening system of claim 6, wherein the first and second optical fibers comprise a single fiber, multiple fibers, or both.

9. The screening system of claim 1, further comprising a collimator operatively coupled to the radiation unit.

10. The screening system of claim 1, further comprising a controller unit configured to control a timing relation between the radiation unit, the scanning unit, and the detection unit.

11. The screening system of claim 1, further comprising a signal processing unit configured to process data acquired by the detection unit.

12. The screening system of claim 1, further comprising a user interface configured to communicate between a user and the screening system.

13. The screening system of claim 1, further comprising a display device to display screening data.

14. The screening system of claim 1, wherein the scanning unit comprises a two dimensional scanning device configured to scan the analysis surface in at least two directions.

15. A screening system configured to screen at least a portion of a biological sample disposed on an analysis surface, comprising:
   a screening module configured for identifying one or more regions of interest in the biological sample, comprising:
      a radiation unit comprising one or more radiation sources configured to generate a radiation beam, wherein each of the one or more radiation sources is not coupled to focusing optics to provide a respective focus-free radiation beam having a wide field of view;
      a scanning unit comprising one or more scanning devices, wherein the one or more scanning devices are configured to rotate in an oscillatory scanning motion about an axis of rotation to scan the analysis surface in at least one direction, wherein the scanning unit is coupled to the radiation unit, and wherein the one or more scanning devices comprise a micro-electro mechanical system (MEMS) scanning device, an electronic-controlled liquid crystal scanning device, an acoustic optical scanning device, or combinations thereof;
      a detection unit comprising one or more detection devices, wherein the detection unit is configured to acquire data representative of one or more constituents of the biological sample;
      a signal processing unit configured to process the data acquired by the detection unit;
      a controller unit configured to control a timing relation between the radiation unit, the scanning unit, and the detection unit; and
   a microscope imaging module operatively coupled to the screening module and configured for performing detailed analysis of one or more of the identified regions of interest.

16. The screening system of claim 15, wherein the microscope imaging module comprises a microscopy imaging unit, another screening module, a laser cytometer, or combinations thereof.

* * * * *